United States Patent [19]

Brame

[11] Patent Number: 4,825,473

[45] Date of Patent: May 2, 1989

[54] DISPOSABLE EYE GUARD

[75] Inventor: William D. Brame, Long Beach

[73] Assignee: Spray Sok Co., Inc., Bellflower, Calif.

[21] Appl. No.: 150,940

[22] Filed: Feb. 1, 1988

[51] Int. Cl.⁴ .......................... A42B 1/00; A42B 1/04
[52] U.S. Cl. ............................................ 2/202; 2/9; 2/206
[58] Field of Search ............... 2/200, 202, 206, 9, 2/4, 239; 66/178 A, 187

[56] References Cited

U.S. PATENT DOCUMENTS

| | | | |
|---|---|---|---|
| 161,003 | 3/1875 | Brugger et al. | 2/205 |
| 766,426 | 8/1904 | Comstock | 2/4 |
| 853,012 | 5/1907 | Grumbar | 2/202 |
| 1,186,703 | 6/1916 | Sullivan | 2/202 X |
| 1,583,872 | 5/1926 | Davis | 2/4 |
| 2,784,409 | 3/1957 | Slipakoff | 2/4 |
| 3,310,966 | 3/1967 | Berry | 66/178 A |
| 3,333,314 | 8/1967 | Harris | 66/178 A |
| 3,505,678 | 4/1970 | Key | 2/4 |
| 3,531,952 | 10/1970 | Chesebro, Jr. | 2/202 X |
| 3,740,767 | 6/1973 | Schuessler | 2/202 X |
| 3,785,173 | 1/1974 | Hanney et al. | 66/187 X |
| 3,789,839 | 2/1974 | Lund et al. | 2/206 X |
| 4,214,318 | 7/1980 | Gomez | 2/4 |
| 4,285,068 | 8/1981 | Ross | 2/202 |
| 4,514,995 | 5/1985 | Curtis et al. | 66/200 |

FOREIGN PATENT DOCUMENTS

| | | | |
|---|---|---|---|
| 068733 | 1/1987 | Japan | 2/243 A |
| 12715 | 7/1916 | United Kingdom | 2/206 |

Primary Examiner—Werner H. Schroeder
Assistant Examiner—Jeanette E. Chapman
Attorney, Agent, or Firm—Glen M. Burdick

[57] ABSTRACT

A disposable protective eye guard positionable over a person's head to protect the person's eyes from airborne particles and spray mist, the eye guard comprising a tubular hood member fabricated of an open mesh knitted fabric having sufficient stretching properties to fit snuggly thereon without distorting the person's facial features. The open mesh knitted fabric has an uneven surface which, when in the stretched condition, cooperates with the person's facial features to provide air pockets between the eye guard and the person's eyes to substantially prevent airborne particles and spray mist from reaching the eyes.

8 Claims, 1 Drawing Sheet

DISPOSABLE EYE GUARD

BACKGROUND OF THE INVENTION

1. Field of the Invention

The present invention relates generally to disposable eye guard apparel, and more particularly, but not by way of limitation, to a disposable eye guard fabricated of an open mesh fabric for protecting a person's eyes from airborne particles and spray mist.

2. Discussion of the Prior Art

Craftsmen are often exposed to airborne particles or spray mist generated during the use of spray guns, the blowing of accoustical ceilings, chipping and the like, especially in the construction and remodelling industries. One of the major concerns has been the protection of the face, head and eyes of such craftsmen from the airborne particles and spray mist.

In an effort to overcome these problems protective hood-type apparel has been provided that fits snuggly over the head to cover a major portion thereof. Such protective hoods, which are generally fabricated of an open mesh material for permitting the skin to breathe for maximum comfort, can be positioned to expose the wearer's eyes, eyes and nose or eyes, nose and mouth. The exposure of the wearer's eyes is required in such prior art devices so that the protective hood does not restrict the wearer's peripheral vision. Thus, in order to protect the eyes of a person wearing such a protective hood, goggles have been employed to protect the person's eyes from the airborne particles and spray mist. One example of a protective hood-type apparel is the Spray Sok ® protective hood manufactured by Spray Sok Co. of Bellflower, Calif. 90706.

While protective hoods such as described above have been successful in protecting a large portion of the wearer's head and skin from airborne particles and spray mist, and when used in combination with goggles have provided temporary protection for the wearer's eyes, problems have nevertheless remained in that the goggles or glasses readily become covered or coated with the spray mist or airborne particulate matter. When the goggles or glasses become coated with such materials one must either shut-down the equipment in order to clean the goggles or glasses, or replace same. This is especially true when using goggles or glasses in spray painting or blowing of accoustical ceilings.

Thus, a need has remained for a disposable eye guard which does not restrict the peripheral vision of the wearer, which permits the skin to breathe for maximum cooling and comfort, which does not require the shutting-down of equipment to clean or replace goggles, and which does not irritate or distort the facial features of the wearer. It is to such a disposable eye guard that the subject invention is directed.

SUMMARY OF THE INVENTION

The present invention relates to an eye guard fabricated of a stretchable knitted fabric positionable over a person's head in an eye covering relationship so that the person's eyes are protected from airborne particles and spray mist. The eye guard comprises a tubular hood member fabricated of an open mesh fabric having sufficient stretching properties such that, when the eye guard is placed over the person's head in an eye covering position the person's facial characteristics are not distorted and the person has substantially unrestricted peripheral vision and movement of the eyelids.

The eye guard has an uneven surface and cooperates with the person's facial features to form air pockets at the person's eyes. These air pockets, in combination with the structure of the eye guard, prevent airborne particles and spray mist from passing through the open mesh fabric into the wearer's eyes. The tubular construction of the eye guard permits the positioning of fresh fabric over the eyes once a previous fabric portion has become substantially saturated with captured airborne particles and spray mist by the rotation of the tubular member on the person's head.

An object of the present invention is to provide an improved eye guard device for protecting a person's eyes from airborne particles and spray mist.

Another object, while accomplishing the before-stated object, is to provide an eye guard device which does not restrict the peripheral vision of the person wearing such a device.

Yet another object of the present invention, while accomplishing the before-stated objects, is to provide an eye guard device which permits freedom of movement of the wearer's eyelids, does not irritate or chaff the skin of the person using the device, and which permits the covered area of the wearer's skin to breathe for maximum cooling and comfort.

Other objects, advantages and features of the present invention will become clear from the following detailed description when read in conjunction with the drawings and the appended claims.

DESCRIPTION

Figure 1:
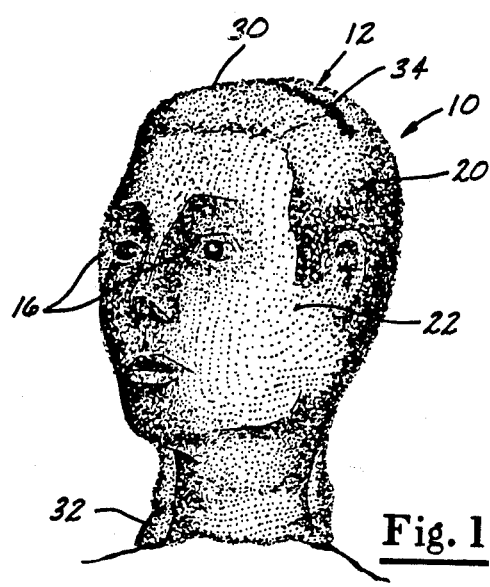
FIG. 1 is a pictorial representation of a person's head upon which is disposed a protective eye guard of the present invention constructed in accordance with the present invention.
Figure 2:
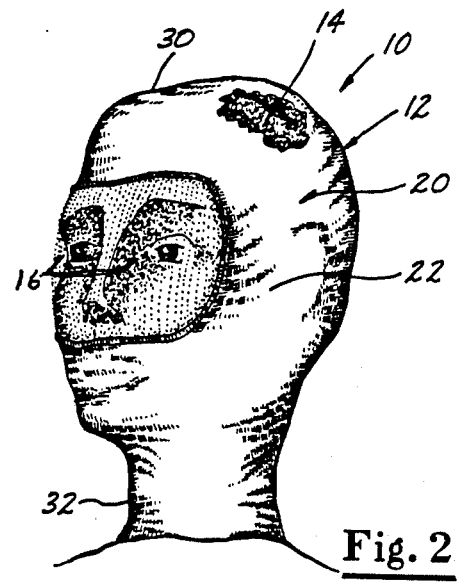
FIG. 2 is a pictorial representation of the person's head wearing the protective eye guard of FIG. 1 in combination with a hood-type apparel having an eye and nose opening therein.

Referring now to the drawings, and more particularly to FIGS. 1 and 2, shown therein is a person's head 10 wearing an eye guard or protective apparel 12 constructed in accordance with the present invention. The eye guard 12 fits snuggly over the head 10 for protecting the person's eyes from airborne particulate matter and spray mist.

The eye guard 12 can be worn as the sole protective device (as illustrated in FIG. 1); or the eye guard 12 can be worn in combination with a protective hood apparel 14 (as illustrated in FIG. 2). It should be noted that the eye protecting properties of the eye guard 12 are not altered whether the eye guard 12 is worn on the head 10 as the sole protective device, or in combination with the protective hood apparel 14. The choice of use of the eye guard 12 with additional protective apparel is determined solely by the desire of the person to prevent spray mist and particulate matter from contacting the person's hair and skin and to aid in clean up after the completion of the work assignment.

As will be described in more detail hereinafter, the unique construction of the eye guard 12, in combination with the person's facial characteristics, provides air pockets 16 between the person's eyes and the portions of the eye guard 12 positioned in an eye covering relationship. The combination of the air pockets 16 and the unique construction of the eye guard 12 substantially prevents airborne particulate matter and spray mist from passing therethrough and entering the person's eyes.

This result is quite unexpected and appears to be unique. That is, in those areas where the eye guard 12 is in contact with the person's skin and no air pocket is developed between the person's skin and the eye guard 12, particulate matter and spray mist can penetrate the surface of the eye guard 12 for deposit on the person's skin. However, when the eye guard 12 and the person's facial characteristics produce the air pocket 16, passage of airborne particulate matter and spray mist therethrough for contact with the person's skin or eyes is substantially eliminated.

It is believed that the unique construction of the eye guard 12 achieves the before-mentioned phenomena of the development of the air pockets 16 in combination with the person's facial characteristics; and that same is accomplished without substantial restriction of the peripheral vision and movement of the person's eyelids. Further, the eye guard 12 does not distort the person's facial characteristics when positioned over the person's head.

Figure 3:
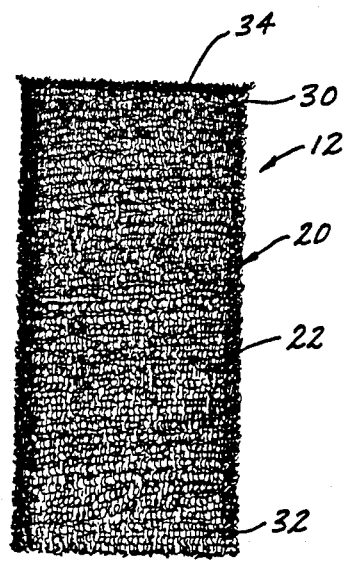
FIG. 3 is an elevational view of the protective eye guard of FIG. 1 illustrating the sealing of one end thereof.

The eye guard 12 is illustrated in FIGS. 1–3 as a hood member 20 having a body portion 22 fabricated of an open mesh fabric having sufficient stretching properties so that upon positioning the hood member 20 over the head 10 the person's facial characteristics are undistorted. The body portion 22 of the hood member 20 defines an uneven external surface 26 (pictorially represented in FIG. 5) when in the stretched condition. The body portion 22 cooperates with the person's facial features to provide the air pockets 16 between the body portion 22 and the person's eyes when worn by the person. The open mesh fabric described more particularly hereinbelow, is constructed such that the external surface (the surface away from the wear's face) of the fabric presents a somewhat rough, unevenly textured surface, as opposed to the smooth surface, for example, of that presented by an ordinary nylon stocking mesh pulled over a person's head for disguises and protective reasons. To the contrary, the open mesh fabric of the hood member 20 should remain substantially open during stretching but yet the uneven weaving disposition of its yarn, or the like, will present circuitous and interrupted traverse of particles attempting to pass therethrough. This prevents substantially unrestricted visibility to the wearer while providing unexpected filtering of unwanted particle passage to the wearer's eyes and face.

As previously stated, the combination of the stretching properties of the body portion 22, the uneven surface area 26 of the body portion 22, and the formation of the air pockets 16 between the person's eyes and the stretched body portion 22 of the hood member 20 substantially prevent the airborne particles and spray mist from passing through openings 28 formed in the open mesh fabric and thus entering the person's eyes. At the same time, the open mesh design of the fabric from which the hood member 20 is produced permits the person to have peripheral vision and unrestricted movement of the eyelids.

The body portion 22 of the hood member 20 is further characterized as having a first end 30 and an opposed second end 32. The first end 30 is desirably sealed by any suitable means, such as by a seam 34 formed using conventional sewing techniques, so that the first end 30 is closed and prevents passage of the person's head 10 through the body portion 22 of the hood member 20. Thus, the hood member 20 is adapted not only to be flexible, but to fit snuggly over the person's head 10 and to substantially conform to the contour thereof.

When sealing the first end 30 of the hood member 20 by a suitable means, such as sewing, one substantially eliminates rough edges which would tend to chaff or irritate the person's head or skin. Further, when employing the tubular construction no additional edges are formed in the body portion 22 of the hood member 20 which would likewise cause any chaffing or irritation of the skin.

The body portion 22 can be provided with varying lengths depending upon the use for which the hood member 20 is intended. For example, if one desires to construct a hood for covering only a person's eyes and nose the hood member 20 will have one length; whereas if one desires, which is preferable, to provide a completely hooded enclosure for a person's face, the body portion 22 will have a length effective to permit the opposed second end 32 of the body portion 22 to be positioned below the chin and cover at least a portion of the neck of the head 10 substantially as shown in FIGS. 1 and 2.

It should further be noted that by fabricating the hood member 20 as a tubular member, the tubular member can be rotated on the person's head 10 for presenting fresh fabric over the eyes once a previous portion has become substantially saturated with captured airborne particles or spray mist. This permits the eye guard 12 to have a longer extended life, improving the efficiency of the wearer in that he or she can readily rotate the hood member 20 to provide fresh fabric over the eyes without shutting-down equipment to clean eye protective devices.

Figure 4:
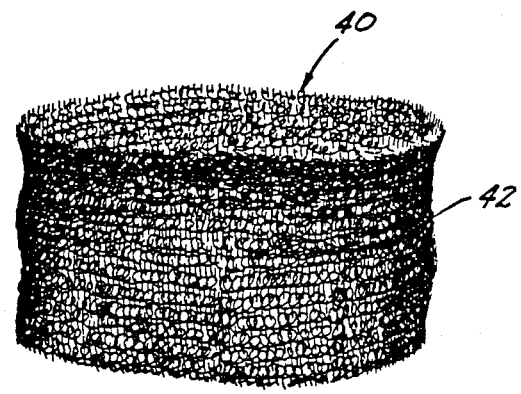
FIG. 4 is a perspective view of a second embodiment of a protective eye guard constructed in accordance with the present invention.

Referring now to FIG. 4 a second embodiment of an eye guard 40 is illustrated. In this embodiment the eye guard 40 is provided with a body portion 42 positionable over the person's head so as to be in a covering relationship with the eyes, and desirably the nose as well. The length of the body portion 42 of the eye guard 40 can vary widely, but should be of sufficient length such that the eye guard 40, when positioned in an eye covering relationship on the person's face, does not have a tendency to roll or curl. Generally, such can be accomplished if the body portion 42 of the eye guard 40 has a length of about four (4) inches or greater. As heretofore discussed with the eye guard 12, the body portion 42 of the eye guard 40 is fabricated as a tubular member and is rotatable on the person's head for presenting fresh fabric over the eyes once a previous portion has become substantially saturated with captured airborne particles and spray mist.

Figure 5:
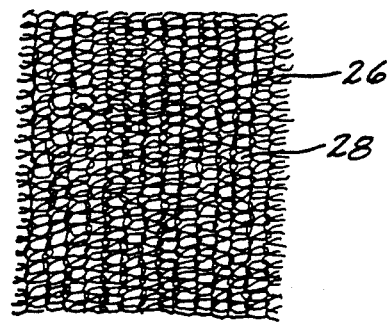
FIG. 5 is a pictorial representation of a portion of an open mesh knitted fabric employed in the construction of the eye guard of the present invention.

Referring now to FIG. 5, the open mesh fabric employed in the fabrication of the hood member 20 of the eye guard 12, and the body portion 42 of the eye guard 40, will be described. It is believed that the unique construction of the open mesh knitted fabric material from which the tubular hood member 20 and the tubular eye guard 40 are fabricated, together with the uneven surface 26 formed during the knitting process of the fabric material, enables the material to create the desired air pockets 16 between the person's eyes and the stretched knitted textile material so as to substantially prevent airborne particles and spray mist from passing through the knitted textile material and the air pockets 16 and into contact with the person's eyes.

The open mesh knitted fabric employed in the fabrication of the eye guards of the present invention is characterized as a one-by-one rib knitted or jersey knitted textile material knitted of a stretch, non-reflective yarn. By employing such a knitting procedure, as well as the use of the stretch, non-reflective yarn, the resulting knitted textile material is provided with the desired uneven surface 26 heretofore mentioned. Further, it is desirable that the non-reflective yarn (i.e. a yarn having a black or beige color) be employed to reduce light reflection which could impair the vision of the craftsmen utilizing the eye guard. An open mesh knitted fabric suitable for the fabrication of the eye guards 12 and 40 of the present invention is manufactured by Murray Fabrics, Inc. of Murray, Ky. as 1/150/33-120 (S. P.) 18–19 inch cross stretched fabric. In addition, such a fabric can be knitted of a textured stretch yarn such as a polyester yarn, nylon yarn, polypropylene yarn and the like.

Experimental use has shown that, when employing an eye guard, either in combination with a protective hood apparel or by itself, the eye guard substantially eliminates airborne particulate material and spray mist from passing through the eye guard and into the wearer's eyes. Thus, clean up of the wearer's face after the completion of a job is substantially eliminated, and watering, burning, irritated eyes are prevented which provides improved health and safety factors for craftsmen exposed to airborne particulate matter and spray mist. Further, the unique design of the eye guard of the present invention provides the eye guard with a desired flexibility so that it can be snuggly fitted on the person's head and at the same time conform to the head of the person, thereby allowing complete freedom of movement of the eyelinds with no rough edges to chaff or irritate the person's skin.

An additional advantage of the unique and novel eye guard of the present invention is that there is peripheral vision. Also, the tubular member forming the eye guard can be rotated on the person's head without removing same therefrom so as to present fresh fabric over the eyes once previous portions have been substantially saturated with captured airborne particles and spray mist. The open mesh design of the eye guard permits the person's skin to breathe for maximum cooling and comfort, and the eye guard substantially eliminates the use of goggles which can become coated with the offending material (i.e. paint, acoustic materials, and the like) whereupon the vision would be completely obscured.

The unique construction of the eye guard from a knitted open mesh fabric knitted of stretch yarn, and its ability to create the air pockets over the person's eyes is not fully understood. However, it appears from actual observation that the eye guard tends to function as a baffle similar to one in a spray booth, collecting airborne particles due to its uneven surface, and since there is no actual air vent, the air pocket is created which prevents air flow. Once air flow is prevented through the air pocket, the airborne particles and spray mist are prevented from passing through the air pocket and thus entering the eyes so as to cause irritation. Further, when desired and for normal safety precautions the eye guard can readily be worn with a conventional respirator to protect the person from breathing in such airborne particles and spray mist.

From the foregoing, it becomes apparent that the eye guard of the present invention is well adapted to carry out the objects and attain the ends and advantages mentioned as well as those inherent therein. It will be understood that numerous changes may be made which will readily suggest themselves to those skilled in the art which are encompassed within the spirit of the invention and as defined in the appended claims.

What is claimed is:

1. An eye guard for protecting a person's eye from airborne particles comprising:

a hood member having a body portion fabricated of an open mesh fabric, the open mesh fabric having sufficient stretching properties so that upon positioning the hood member over the person's head the person's facial characteristics are undistorted and air pockets are formed between the body portion and the person's eyes, the open mesh fabric presenting an uneven, textured external surface so that airborne particles are substantially prevented from passing through the open mesh fabric to reach the person's eyes while permitting visibility therethrough.

2. A disposable protective apparel positionable over a person's head to protect the person's eyes from airborne debris, the protective apparel comprising:

a tubular hood fabricated of an open mesh fabric material having sufficient stretching properties to fit snuggly over the person's head without distorting the person's facial features and providing air pockets over the eyes so that the person has substantially unrestricted movement of the eyelids when the tubular hood is positioned in an eye covering position, the open mesh fabric material knitted to have an uneven, textured external surface in its stretched condition so that visibility is provided therethrough and so that airborne particles are substantially prevented from passing through the stretched open mesh fabric material; and means for sealing one end of the tubular hood so that the sealed end thereof substantially conforms to the top portion of the person's head.

3. The eye guard of claim 1 wherein the hood member is a tubular member and the tubular member is rotatable on the person's head for presenting fresh fabric over the eyes once a previous portion has become substantially saturated with captured airborne particles.

4. The eyeguard of claim 3 wherein the tubular member is characterized as having a first end and wherein the eyeguard further comprises:

closure means for closing the first end of the tubular member to prevent passage of the person's head therethrough.

5. The eye guard of claim 4 wherein the open mesh fabric is knitted of a non-reflective stretch yarn, wherein the tubular member is further characterized as having an opposed second end, and wherein the length of the body portion is such as to dispose the opposed second end thereof below the person's chin when stretched over the peron's head.

6. The disposable protective apparel of claim 2 wherein the open mesh fabric is characterized as a one-by-one rib knitted textile material knitted of a stretch, non-reflective yarn, the knitted textile material providing an uneven surface so that in the stretch condition the stretched fabric substantially prevents airborne from passing through the knitted textile material and the air pockets to reach the person's eyes.

7. The disposable protective apparel of claim 6 wherein the tubular hood has a length such that an opposed second end thereof is positionable below the person's chin.

8. The disposable protective apparel of claim 7 wherein the tubular hood is rotatable on the person's head for altering the eye covering portion thereof presenting fresh fabric over the eyes once a previous portion has become substantially saturated with captured airborne debris.

* * * * *